(12) United States Patent
Griffin et al.

(10) Patent No.: US 7,744,371 B1
(45) Date of Patent: Jun. 29, 2010

(54) ADJUSTABLE HVE TIP

(75) Inventors: Bradley P. Griffin, Greenville, NC (US); Jonathan Mang, Hong Kong (CN)

(73) Assignee: Practicon, Inc., Greenville, NC (US)

( * ) Notice: Subject to any disclaimer, the term of this patent is extended or adjusted under 35 U.S.C. 154(b) by 0 days.

(21) Appl. No.: 11/974,621

(22) Filed: Oct. 15, 2007

(51) Int. Cl.
*A61C 17/08* (2006.01)

(52) U.S. Cl. .......................... 433/91; 433/95; 604/902; 285/181; 285/184

(58) Field of Classification Search ............. 433/91–96; 604/93.01, 264, 275, 543, 902, 35, 22; 285/184, 285/148.4, 275, 279, 280, 181
See application file for complete search history.

(56) References Cited

U.S. PATENT DOCUMENTS

| | | | | |
|---|---|---|---|---|
| 39,700 | A * | 8/1863 | Morrison | 285/181 |
| 327,877 | A * | 10/1885 | Hodges | 285/184 |
| 597,469 | A * | 1/1898 | Marshall | 433/124 |
| 950,109 | A | 2/1910 | Levkowicz | |
| 1,774,986 | A * | 9/1930 | MacKenzie | 285/280 |
| 2,274,893 | A * | 3/1942 | Hyman | 433/91 |
| 2,503,281 | A * | 4/1950 | Lynch et al. | 285/181 |
| 2,519,595 | A | 8/1950 | Older | |
| 2,581,047 | A * | 1/1952 | Salmond et al. | 285/181 |
| 2,587,170 | A * | 2/1952 | Klingler et al. | 285/279 |
| 3,084,439 | A * | 4/1963 | Staunt | 433/104 |
| 3,863,635 | A * | 2/1975 | Swatman | 604/119 |
| 4,221,220 | A * | 9/1980 | Hansen | 604/119 |
| 4,417,874 | A | 11/1983 | Andersson et al. | 433/96 |
| 4,586,900 | A * | 5/1986 | Hymanson et al. | 433/96 |
| 4,807,370 | A | 2/1989 | Trimble | 33/529 |
| 4,872,837 | A * | 10/1989 | Issalene et al. | 433/29 |
| 4,878,900 | A * | 11/1989 | Sundt | 604/119 |
| 5,106,300 | A * | 4/1992 | Voitik | 433/173 |
| 5,425,637 | A | 6/1995 | Whitehouse et al. | 433/95 |
| 5,549,634 | A * | 8/1996 | Scott et al. | 606/170 |
| 5,688,121 | A | 11/1997 | Davis | 433/91 |
| 5,743,736 | A | 4/1998 | Folko et al. | 433/96 |
| 6,299,444 | B1 | 10/2001 | Cohen | 433/91 |
| 6,561,549 | B1 * | 5/2003 | Moris et al. | 285/184 |
| 6,602,072 | B2 | 8/2003 | Burney | 433/96 |

(Continued)

FOREIGN PATENT DOCUMENTS

DE     43 06 450 A1     5/1994

(Continued)

OTHER PUBLICATIONS

Photographs of prior art HVE tips.

*Primary Examiner*—Ralph A Lewis
(74) *Attorney, Agent, or Firm*—K&L Gates LLP

(57) ABSTRACT

A HVE tip that includes two tubular members, each of which is formed with a straight portion and a connecting portion, and one of the connecting portions is telescopically received within the other connecting portions so that the two tubular members can be rotated relative to one another between a plurality of configurations, including a straight configuration in which the axes of the two straight portions of the two tubular members extend generally parallel to one another and in the same plane, and a right angle configuration at which these axes extend generally perpendicular to one another in the same plane. An indexing connection is provided between the two connecting portions.

2 Claims, 5 Drawing Sheets

U.S. PATENT DOCUMENTS

| | | | |
|---|---|---|---|
| 2003/0134254 A1 | 7/2003 | Filho | 433/96 |
| 2005/0004520 A1 | 1/2005 | Lemoine et al. | 604/118 |
| 2006/0088800 A1* | 4/2006 | Neff et al. | 433/91 |
| 2008/0265565 A1* | 10/2008 | Sitz et al. | 285/98 |

FOREIGN PATENT DOCUMENTS

| | | |
|---|---|---|
| EP | 000390951 A1 | 10/1990 |
| JP | 02002165816 A | 6/2002 |

* cited by examiner

ADJUSTABLE HVE TIP

BACKGROUND OF THE INVENTION

The present invention relates generally to dental equipment used to evacuate from a patient's mouth liquids, residues, aerosols, and debris created as a by-product of many dental procedures, and more particularly to a tip used in conjunction with high volume evacuation (HVE) equipment.

Many dental procedures generate from within the patient's mouth a significant amount of infectious waste in the form of airborne fluids, or aerosols, and solid debris. It is important that this waste be captured and evacuated in order to control the biological contamination of the operatory and the well-known health risks associated therewith. In addition, the liquids and residues that collect within the patient's mouth should be continuously removed to improve the comfort of the patient, the visibility of the operating field and the integrity of the dental procedure, the latter of which is often compromised by excess moisture. Therefore, as is well known in the art, HVE systems are used to remove liquids, residues, aerosols, and debris, and these systems typically include a vacuum source, a hand held device, typically a manual valve that is connected to the vacuum source, and a tip that is removably mounted in the hand held device. In use, the dental technician holds the hand held device in a manner that inserts the HVE tip into the patients mouth, and locates the open end of the tip at the point where it will be most effective in removing the by-products generated by the particular dental procedure.

It is important that the HVE tip not be positioned where it will interfere with the dental procedure, and it is also important that the HVE tip be positioned so that it will be as comfortable as possible for both the patient and dental technician holding and manipulating the hand held device. Further, as the tip is often used to retract the patient's tongue and cheek to increase intraoral visibility and access during the procedure, it is important that the HVE tip be rigid in order to continuously exert the necessary force for retraction. Most HVE tips comprise either a tubular member that extends in a straight line that makes it generally easier for the dental technician to locate the open end of the tubular member at the exact location desired in certain dental procedures, or a tubular member that includes a rigid bend or angle to assist in properly locating the tip during other dental procedures and that improves the ergonomics and comfort of the dental technician. In either case, it is not possible to change the configuration of the HVE tip from its rigid straight or bent configuration, and it is therefore not possible for the dental technician to be able to take advantage of the straight configuration when it needed and to also be able to take advantage of the bent configuration when it would be more desirable.

Some efforts have been made to make HVE tips adjustable. For example, in Lemoine U.S. Patent Application Publication 2005/0004520, a hand held device in a HVE system is constructed to allow the end of the handheld device on which the HVE tip is located to rotate. While this arrangement makes it possible to change the rotational position of the tip relative to the hand held device, it is not possible to change the angle of the tip. In Levkowicz U.S. Pat. No. 950,109, a low volume saliva ejector is provided that permits parts of the tubular member to rotate and slide relative to one another, but the tubular member is bent at a plurality of sharp angles that inherently interferes with the smooth flow of liquid and debris therethrough, and the movable, slidable parts do not lend themselves to quickly and easily providing both a straight configuration and a right angle configuration.

Therefore, there is a need for HVE tips that are simultaneously adjustable and rigid, and that can be quickly and easily configured in either a generally straight configuration or a right angle configuration, as well as a plurality of other configurations, all of which result in a HVE tip that is easy to use and versatile in providing a variety of configurations that can be used effectively in a variety of dental procedures.

SUMMARY OF THE INVENTION

The present invention provides an adjustable HVE tip which includes a first tubular member having a first generally straight primary portion and a first connection portion formed integrally with the first primary portion and extending away therefrom at a predetermined angle. A second tubular member is also provided which has a second generally straight primary portion and a second connection portion formed integrally with the second primary portion and extending away therefrom at an predetermined angle. One of the first and second connection portions is telescopically received within the other connection portion and is rotatable relative thereto to permit the first and second primary portions to be adjustably positioned relative to one another at a plurality of predetermined positions, including a first position at which the axes of the first and second primary portions extend in generally parallel relation to one another and in the same plane and a second position at which the axes of the first and second primary portions extend in generally perpendicular relation to one another and in the same plane.

In the preferred embodiment of the present invention, the first connection portion extends away from the first primary portion at an obtuse angle, preferably an angle of 135 degrees, and the second connection portion also extends away from the second primary portion at an obtuse angle which is preferably 135 degrees. Also, in the preferred embodiment, one of the connecting portions is provided with a plurality of protrusions and the other connecting portion is formed with a plurality of slots for engaging the protrusions to provide an indexing connection between the first and second tubular members.

Finally, the exterior surface of the connecting portion of first tubular member may be formed with a plurality of indentations to facilitate grasping the first tubular member during the relative rotation of the first and second tubular members, and the exterior surface of the open end of the straight portion of the first tubular member may be formed with a slight outwardly flared taper and may have a textured surface configuration.

DESCRIPTION OF THE PREFERRED EMBODIMENT

Figure 1:
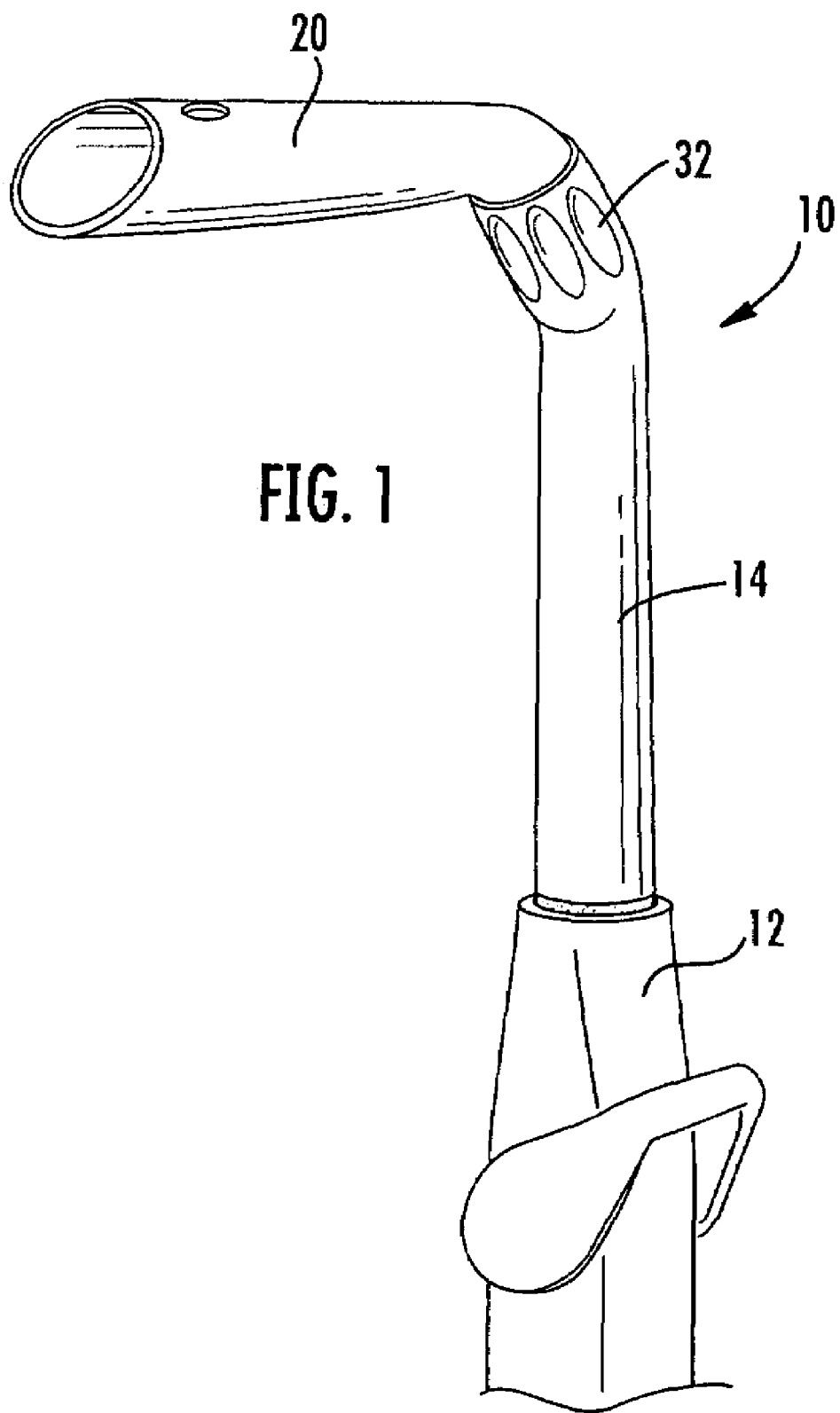
FIG. 1 is a perspective view of an HVE tip according to present invention which is mounted in a hand-held device.

Looking now in greater detail at the accompanying drawings, FIG. 1 illustrates a HVE tip 10 which is constructed in accordance with the present invention, and which is mounted in a representative and conventional handheld device 12 which forms no part of the present invention.

Figure 2:
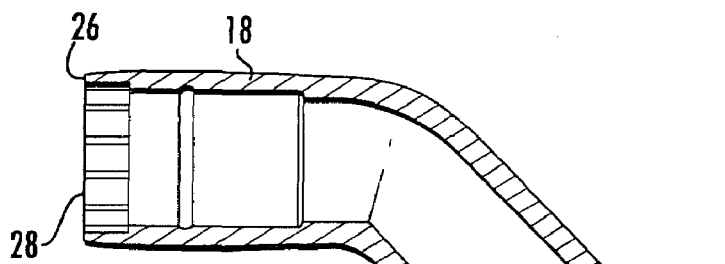
FIG. 2 is a cross-sectional view taken through the center of one of the tubular members forming part of the HVE tip.
Figures 5, 6:
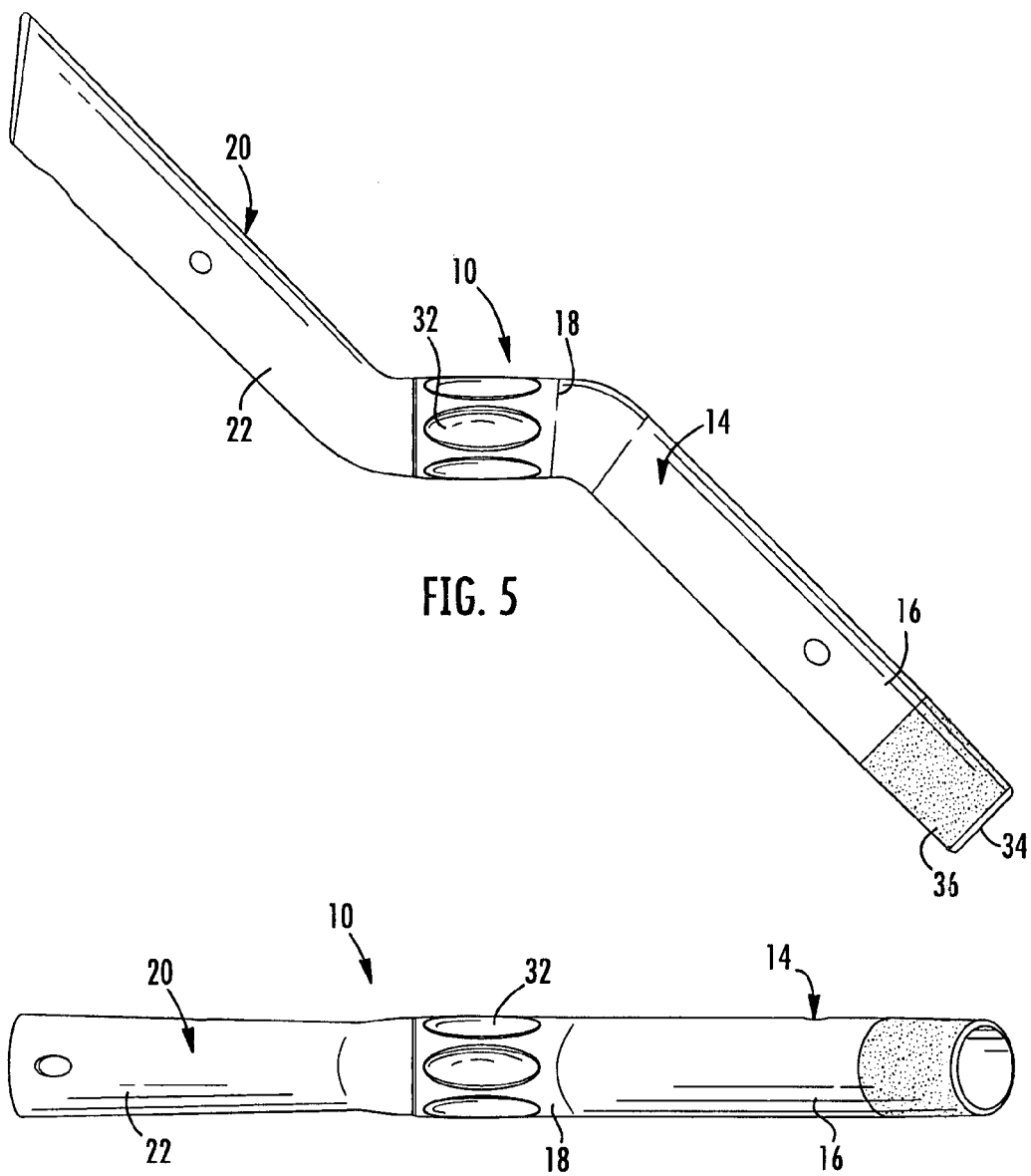
FIG. 5 is a plan view of the HVE tip of the present invention in one of its configurations.
FIG. 6 is a side view of the HVE tip illustrated in FIG. 5.

As best seen in FIGS. 2, 5 and 6, the HVE tip 10 includes a first tubular member 14 which has a generally straight primary portion 16 and a connecting portion 18 that is formed integrally with the straight portion 16, and extends away from the straight portion 16 at a predetermined obtuse angle, which is preferably 135 degrees.

Similarly, the HVE tip 10 includes a second tubular member 20 that has a generally straight primary portion 22, and a connecting portion 24 that is formed integrally with the straight portion 22 and extends away therefrom at a predetermined obtuse angle, preferably about 135 degrees.

Figure 3:
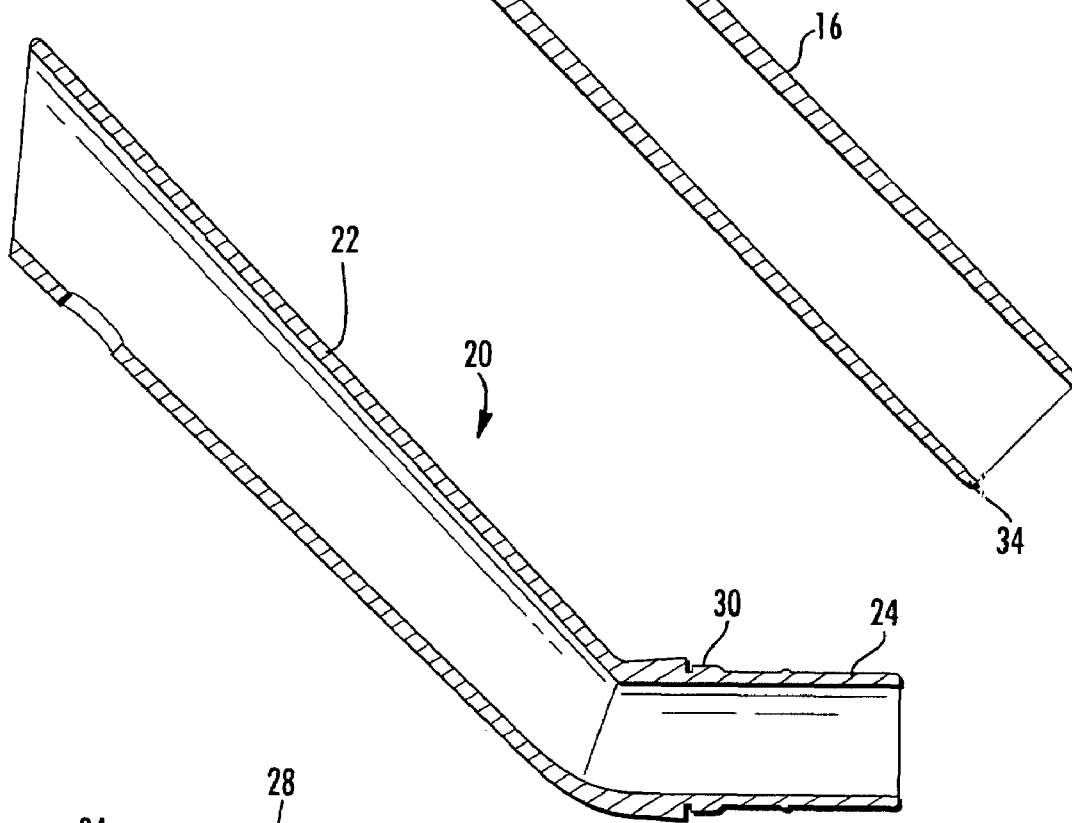
FIG. 3 is a cross-section view taken through the center of the other tubular member forming part of the HVE tip.
Figure 4:
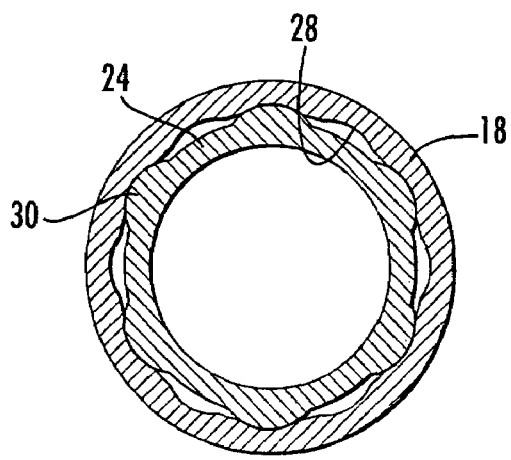
FIG. 4 is a cross-sectional view taken vertically through the connecting portions of the two tubular members and illustrating the indexing connection between the tubular members.
Figure 7:
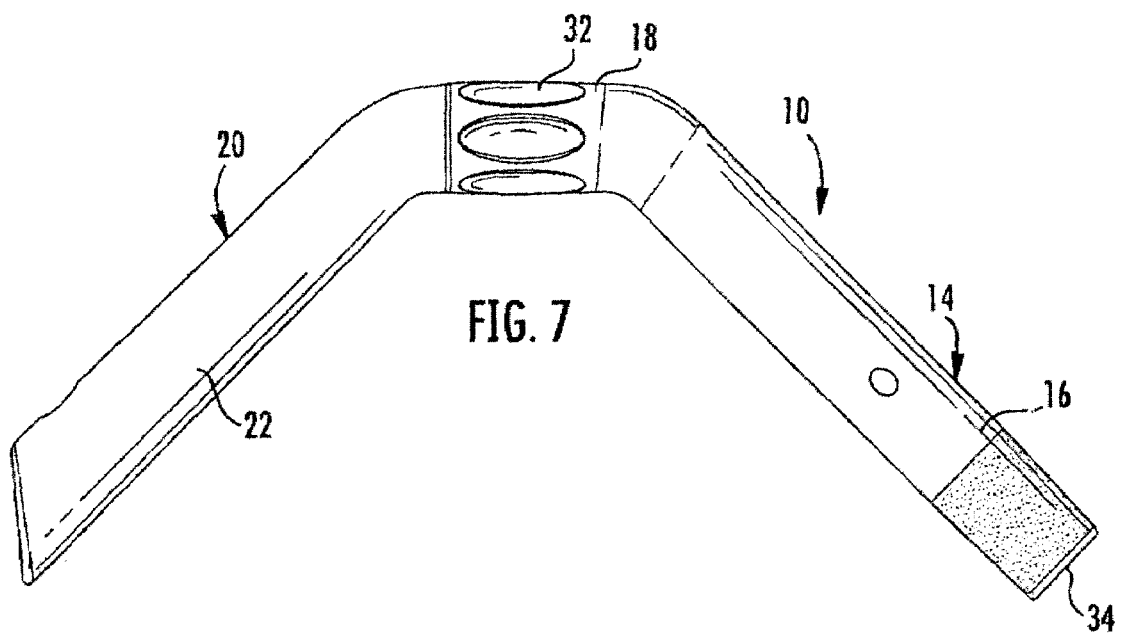
FIG. 7 is a plan view of the HVE tip of the present invention in its right angle configuration.

As best seen in FIGS. 4, 5 and 7, the connecting portion 24 of the second tubular member 20 is telescopically received within the connecting portion 18 of the first tubular member 14 so that the tubular members 14 and 20 are rotatable relative to one another to permit the straight portions 16 and 22 to be adjustably positioned relative to one another at a plurality of predetermined positions, as will be described in greater detail below. As best seen in FIGS. 2, 3 and 4, the open end 26 of the connecting portion 18 is formed with a plurality of slots 28 arranged in a circular pattern on an interior wall of the open end 26. The outer surface of the connection portion 24 is formed with a plurality of protrusions 30 as illustrated in FIG. 3, and when the connecting portion 24 is telescopically received within the connecting portion 18, the slots 28 engage the protrusions 30 as best seen in FIG. 4 to provide an indexing connection between the first and second tubular members 14 and 20.

As best seen in FIGS. 5 and 7, the exterior surface of the connecting portion 18 is formed with a plurality of indentations 32 that are arranged in a circular pattern. These indentations facilitate the grasping of the first tubular member 14 by the user of the HVE tip 10 so that it can be held in place while the second tubular member 20 is rotated about the axes of the telescopically connected connecting portions 18 and 24.

Finally, the exterior surface of the straight portion 16 is preferably formed with a slight taper at the end 34 of the straight portion that is opposite the end connected to the connecting portion 18, and this taper flares outwardly so that when the end of the straight portion 16 is inserted into the open end of the hand held device 12 it will provide a secure fit between the hand held device 12 and the HVE tip 10. In connection with some uses of the HVE tip, it is used to retract the cheek of the patient, and this secure fit between the FIVE tip and hand held device 12 prevents any rotation of the HVE tip relative to the hand held device 12 that might adversely effect the ability of the HVE tip 10 to retract the cheek of the patient. Moreover, the taper also permits the user to remove the HVE tip from the hand held device 12 without too much resistance. The secure fit between the hand held device 12 and the HVE tip 10 may also be enhanced by forming the exterior wall portion at the open end of the straight portion 16 with a textured surface configuration 36.

In use, the HVE tip 10 of the present invention is very versatile and easy to use. The user of the HVE tip 10 can grasp the FIVE tip with one hand using the indentations 32 on the first tubular member 14, and, with the other hand, rotate the second tubular member 20 about the center axes of the connecting portions 18 and 24. The above-described indexing connection formed by the slots 28 and the protrusions 30 allow this relative rotation between the first and second tubular members 14 and 20, but also provide a large plurality of positions (preferably 12, at which the protrusions 30 are located within indentations 32 to temporarily fix the location of one tubular member relative to the other. The wide range of adjustable positions of the first and second tubular members 14 and 20 is illustrated in FIG. 9.

In normal usage, during certain dental procedures, it is desirable to have a HVE tip that has a straight or "bayonet" configuration which will permit the user of the HVE tip to locate the open end of the HVE tip at the desired location within the patient's mouth. However, in other situations, it is preferable to have a HVE tip that has an angular configuration, preferably a right angle configuration, which permits the user to hold and manipulate the handheld device 12 with less fatigue and less strain on the wrist by reducing hose tension and drag. Heretofore, it has not been possible to obtain both of these desired configurations using a single HVE tip.

Figure 8:
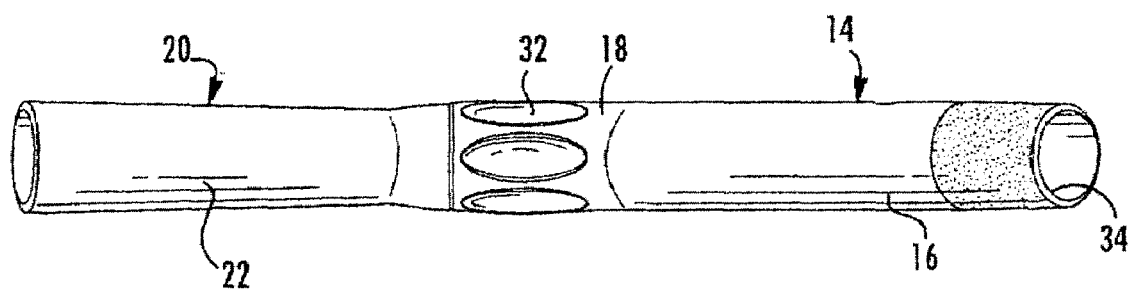
FIG. 8 is a side view of the HVE tip illustrated in FIG. 7.
Figure 9:
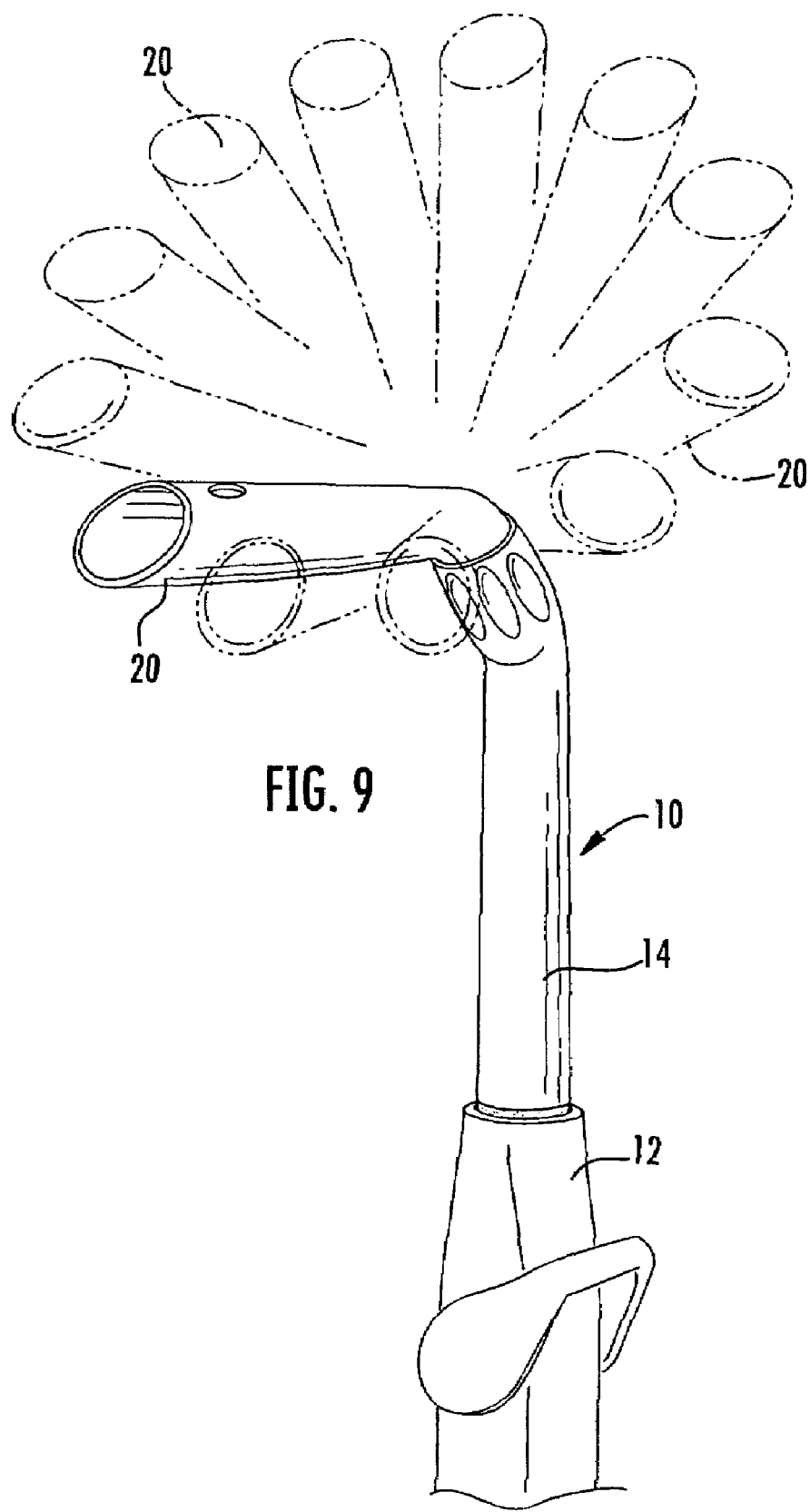
FIG. 9 is a detail view of the HVE tip of the present invention illustrating a plurality of adjusted positions of the tubular members.

However, by a virtue of the versatility of the HVE tip 10 of the present invention, the user is able to quickly and easily adjust the configuration of the HVE tip 10 between a straight configuration and a right angled configuration, and a wide variety of other configurations as illustrated in FIG. 9. More specifically, FIGS. 5 and 6 illustrate the HVE tip 10 in its straight configuration, and it will be noted that the first and second tubular members 14 and 20 are rotated about their respective connecting portions 18 and 24 until the axis of the generally straight portion 16 tubular member 14 and the axis of the generally straight portion 22 of the tubular member 20 extend in generally parallel relation to one another, anti the straight portions 16 and 22 and their respective axes lie in the same plane as best illustrated in FIG. 6. When it is desired to adjust the configuration of the HVE tip 10 to a right angled position that is illustrated in FIGS. 7 and 8, the user simply rotates the second tubular member 20 180 degrees so that the HVE tip 10 assumes the right angled configuration illustrated in FIG. 7. It will be noted that in the right angled configuration, the axis of the straight portion 16 of the tubular member 14 extends at an angle of 90 degrees with respect to the axis of the straight portion 22 of the other tubular member 20, and both of the straight portions 16 and 22 and their axes are located in the same plane as illustrated in FIG. 8. Finally, because of the indexing connection described above, the relative positions of the first and second tubular members 14 and 20 will be rigidly maintained unless and until the user exerts a small amount of force to rotate the tubular members 14 and 20 relative to one another, and the indexing connection will also maintain the relative position of the tubular members 14 and 20 at each of the large plurality of positions as illustrated in FIG. 9. Finally, it will be noted that in both the straight configuration and the right angle configuration, there is little resistance to the flow of liquid and debris through the HVE tip 10. Thus, looking at FIG. 5, the fact that the straight portions 16 and 22 extend away from the connecting portions 18 and 24, respectively, at an angle of 135 degrees results in the flow through the FIVE tip 10 not having to negotiate any sharp turns that could retard the flow. Moreover, even in the right hand configuration (see FIG. 7), the flow does not have to negotiate any right angle turns that would retard flow.

In addition to the advantages pointed out above, the HVE tip 10 of the present invention also provides improved evacuation by the dental technician since it allows the hose (not shown) connected to the handheld device 20 to immediately slope downwardly from the working field for maximum suction efficiency at some of the adjusted positions of the FIVE tip 10. There is also some improved visibility for the dental technicians in that the offset angles of the tubular members 14 and 20 permits the dental technician to keep his or her hands out of the way of the working field. The adjustable design of the HVE tip also accommodates either right or left handed dental technicians with all configurations being available in an opposing symmetrical form.

In view of the aforesaid written description of the present invention, it will be readily understood by those persons skilled in the art that the present invention is susceptible of broad utility and application. Many embodiments and adaptations of the present invention other than those herein described, as well as many variations, modifications, and equivalent arrangements, will be apparent from or reasonably suggested by the present invention and the foregoing description thereof, without departing from the substance or scope of the present invention. Accordingly, while the present invention has been described herein in detail in relation to preferred embodiments, it is to be understood that this disclosure is only illustrative and exemplary of the present invention and is made merely for purposes of providing a full and enabling disclosure of the invention. The foregoing disclosure h; not intended nor is to be construed to limit the present invention or otherwise to exclude any such other embodiments, adaptations, variations, modifications and equivalent arrangements, the present invention being limited only by the claims appended hereto and the equivalents thereof.

What is claimed is:

1. An adjustable HVE tip which includes:
   (a) a first tubular member having a first generally straight cylindrical primary portion with one end thereof being adapted to be mounted in a dental evacuation system and having a first connection portion formed integrally with the other end of the first primary portion and extending away therefrom at an angle of about 135 degrees, the first primary portion having a plurality of shaped indentations formed in a circular pattern in the exterior surface thereof to facilitate grasping the first primary portion in the shaped indentations, and the first connection portion having a plurality of slots formed in a circular pattern in an interior surface thereof;
   (b) a second tubular member having a second generally straight cylindrical primary portion and having a second connection portion formed integrally with one end of the second primary portion and extending away therefrom at an angle of about 135 degrees, the second connection portion having a plurality of protrusions formed in a circular pattern in an exterior surface thereof; and
   (c) the second connection portion being telescopically received within the first connection portion and rotatable relative thereto to permit the first and second primary portions to be adjustably positioned relative to one another at a plurality of predetermined positions, including a first position at which the axes of the first and second primary portions extend in generally parallel relation to one another and in the same plane and a second position at which the axes of the first and second primary portions extend in generally perpendicular relation to one another and in the same plane, and the protrusions in the circular pattern on the second connecting portion being disposed within at least some of the slots in the circular pattern in first connection portion to temporarily fix the location of the first and second connecting portions at said plurality of predetermined positions and thereby provide an indexing connection between the first and second connecting portions.

2. An adjustable HVE tip as defined in claim 1 wherein the exterior surface of the open end of first tubular member is formed with a slight outwardly flared taper, and such exterior surface is textured.

\* \* \* \* \*